United States Patent [19]

Findley et al.

[11] Patent Number: 4,892,830
[45] Date of Patent: Jan. 9, 1990

[54] ENVIRONMENTALLY CONTROLLED IN VITRO INCUBATOR

[75] Inventors: William Findley; William E. Gibbons, both of Houston, Tex.

[73] Assignee: Baylor College of Medicine, Houston, Tex.

[21] Appl. No.: 36,061

[22] Filed: Apr. 2, 1987

[51] Int. Cl.[4] .............................................. C12M 1/38
[52] U.S. Cl. ........................................ 435/290; 236/3; 237/14
[58] Field of Search .................... 236/3; 237/1 R, 14; 435/290; 119/37; 312/1

[56] References Cited

U.S. PATENT DOCUMENTS

| | | | |
|---|---|---|---|
| 3,955,317 | 5/1976 | Gudin | 435/284 |
| 4,111,753 | 9/1978 | Folsom et al. | 195/126 |
| 4,301,252 | 11/1981 | Baker | 435/290 |
| 4,572,427 | 2/1986 | Selfridge | 236/3 |

OTHER PUBLICATIONS

Chetkowski et al., J. In Vitro Fertilization and Embryo Transfer, vol. 2, p. 207 (Sep. 1985).
Auerbach & Brinster, Nature, vol. 217, p. 465 (Feb. 1968).
Wright et al., J. Anim. Sci., vol. 42, p. 912 (Nov. 1976).
Brackett & Wililams, Fertil. Steril., vol. 19, p. 144 (Nov. 1968).
Gwatkin & Haidri, J. Reprod. Fert., vol. 37, p. 127 (Sep. 1974).
Quinn & Harlow, J. Exp. Zool., vol. 206, p. 73 (May 1978).
Tervit et al., J. Reprod. Fert., vol. 30, p. 493 (Apr. 1972).

*Primary Examiner*—Henry A. Bennet
*Attorney, Agent, or Firm*—Davis Hoxie Faithfull & Hapgood

[57] ABSTRACT

An environmentally controlled incubator is described in which the enclosure of the incubator chamber strongly attenuates the transmission of light having wavelengths below about 500 nm for protecting biological materials within the chamber from toxic effects of short wavelength light. The incubator also includes sensors for determining the oxygen and carbon dioxide concentration within the chamber and means for adding carbon dioxide, nitrogen or oxygen to the ambient gas within the incubator ion order to maintain the desired levels of carbon dioxide and oxygen. A thermostatically controlled heater and a humidification chamber warm and humidify the gas as it is circulated through the humidification chamber under control of a fan. An airlock is provided to allow biological materials to be placed within or removed from the chamber.

19 Claims, 3 Drawing Sheets

ENVIRONMENTALLY CONTROLLED IN VITRO INCUBATOR

FIELD OF THE INVENTION

This invention relates generally to incubators for providing a controlled environment for maintaining cells, tissues and organisms in vitro during examination and manipulation, and more particularly to incubators in which the atmosphere and ambient light are controlled to eliminate conditions which may be toxic to such cells, tissues and organisms.

BACKGROUND

Advances in vitro fertilization ("IVF") techniques have raised hopes for its widespread use in permitting infertile human patients to bear children, and hold promise for significant commercial benefits in animal breeding. A problem that has prevented the more widespread use of IVF, however, is the disappointingly low pregnancy rates that have been achievable through the technique, even with the transfer of several preembryos. With humans such rates seldom reach 28% and the ongoing pregnancy rate is usually well below 22%.

Y. Hirao and R. Yanagimachi have reported in their article entitled *Detrimental Effect of Visible Light on Meiosis of Mammalian Eggs In Vitro*, J. Exp. Zool. v. 206, p.365 (1978) that short wavelength visible light (below about 480 nm) emitted from fluorescent lights of the type widely used in laboratories can inhibit the maturational changes (meiosis) which an egg must undergo before fertilization can occur.

Other articles, such as *Effect of Room Florescent Light on the Deterioration of Tissue Culture Medium* by R. L. Wang at page 19 of In Vitro, v. 12 n. 1 (1976), reports that tissue culture medium of the type used in cloning cell lines deteriorates more rapidly when subjected to fluorescent light.

The article *Apparatus For the In Vitro Fertilization and Culture of Human Oocytes* by J. Testart et al at pg. 372 of Fertility and Sterility, v. 38, n.3 (September 1982), acknowledges, as have others, that IVF of mammalian eggs should be carried out under conditions as close as possible to those occurring in vivo. The article describes an incubator in which oocytes and zygotes are maintained in culture tubes stored in metal buckets so as to remain in darkness except when being manipulated or examined. A filtered light source for use with a compound microscope in the incubator is described in which the filter restricts the illumination to the longer wavelength, on the order of 500 to 750 nm, which the article states do not harm mammalian eggs. No filter is used however with the light source extending into the incubator for a steriozoom microscope. In addition, the biological materials are exposed to ambient light each time they are removed from the buckets.

The incubator described in the Testart et al article also provides a controlled atmosphere for the culture media in the culture tubes by bubbling a controlled gas mixture (5% $CO_2$, 5% $O_2$, 90% $N_2$) from a commercially available premixed gas cyclinder through a bottle of distilled water and distributing the humidified gas through a series of culture tubes. The tubes are stoppered and the gas is conducted from tube to tube by tubing extending through holes in the stoppers. However, any examination of the biological materials performed outside of the culture tubes results in their exposure to air.

An article entitled *Development of One-Cell Ovine Embryos In Two Culture Media Under Two Gas Atmospheres* by Betterbed et al, at page 547 of Theriogenology, v. 23, n.3(March 1985), reported experiments in which one-cell and two-cell sheep "embryos" were cultured in either 5% or 20% $O_2$. The article stated that the reduction of oxygen from 20% to 5% had no effect on embryo development.

Earlier work reported by W. K. Whitten in a paper entitled *Nutrient Requirements for the Culture of Preimplantation Embryos In Vitro* given at a symposium in April 1970 in Venice and included in a book entitled Advances in Biosciences published by Pergamon Press found that a higher percentage of mouse embryos reached the blastcocyst stage when cultured in an atmosphere containing 5 to 10% oxygen concentration than when cultured in higher or lower ambient oxygen concentrations.

Applicants have also observed the toxic effects of oxygen concentration of greater than 10%. Applicants have extended such findings to show that exposures to 20% oxygen, the oxygen concentration of air, for as little as two hours or less can also result in toxicity.

In addition, applicants have shown that short wavelength light as well as atmospheric oxygen concentrations is also toxic to mammalian zygotes and pre-embryos. It is believed that the short wavelength light, such as produced by fluorescent lights, and atmospheric concentrations of oxygen adversely effect both the culture medium and the zygotes and pre-embryos themselves. This phenomenon has not previously been observed in human zygotes and pre-embryos since viable pre-embryos are normally replaced in the patient after two or three divisions, while the deterioration does not become apparent until after about 3 or more divisions.

The above referenced Testart et al article in Fertility and Sterility provides a partial but unsatisfactory solution to the above noted problems. Storing the culture tubes in the dark buckets reduces the exposure to short wavelength florescent light and the controlled atmosphere within the culture tubes prevents the exposure to toxic levels of oxygen while a culture is maintained in the tube.

Using the system, however, a culture is exposed to ambient florescent light whenever the culture tube is removed from the bucket. Additionally, the use of culture tubs strung together by gas supply tubing is a particularly inconvenient and disfavored way to maintain cultures which has not found wide acceptance. It is preferred by most researchers, particularly in the United States, to maintain the zygotes and pre-embryos in culture dishes which are easier to manipulate.

SUMMARY OF THE INVENTION

In accordance with the invention there is provided an incubator for use in maintaining and examining cells, tissues and organisms including mammalian eggs, zygotes and pre-embryos in culture media which includes an environmentally closed chamber having an enclosure, a portion of which is transparent to light having a wavelength above about 500 nm and which incorporates filter means for strongly attenuating transmission of shorter wavelength light. Control means are provided for maintaining the oxygen concentration within the chamber at a level substantially lower than in air.

The incubator in accordance with the invention may further include a microscope stand and an aperture in the enclosure for permitting a microscope positioned on said stand to extend through said aperture, and cuff means for sealing between the microscope and said aperture.

In accordance with a further aspect of the invention the incubator may include an airlock which may have a sliding tray therein for permitting objects, such as culture dishes to be placed within or removed from the incubator during use without contaminating the atmosphere within the incubator with air. According to the invention such airlock may include means for coupling thereto a source of gas for controlling the composition of the gas within the airlock.

These and other advantages and features of the invention can be more fully understood from the following detailed description of the preferred embodiment of the invention illustrated in the accompanying drawings.

DESCRIPTION OF PREFERRED EMBODIMENT

Figure 1:
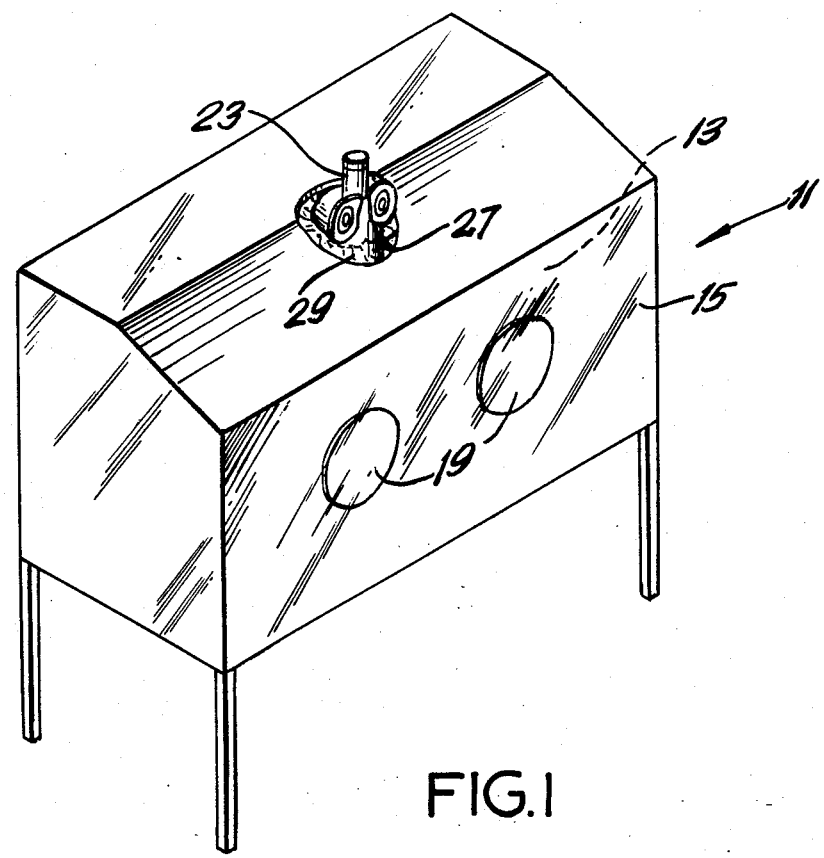
FIG. 1 is an isometric view of an incubator in accordance with the invention.

Referring now to FIG. 1 of the drawings, there is generally illustrated an incubator 11 in accordance with the invention. The incubator 11 includes a chamber 13 which is enclosed by a transparent enclosure 15. The enclosure 15 is formed of transparent sheet material which is formulated to block transmission of short wave length light of the type produced by florescent lighting commonly used in laboratories. Preferably the material of the enclosure 15 is chosen to transmit light only with a wave length greater than about 500 nm and may be, for instance, amber Plexiglass #2422 manufactured by Rohm and Haas, Inc., Bristol, Pennsylvania. The amber Plexiglass strongly attenuates the shorter wave length ambient light and so protects culture media and biological materials within the chamber 13 from toxic effects of short wave length light. The particular wavelength at which the material of the enclosure 15 begins to strongly attenuate light transmission may be selected in accordance with sensitivity of the particular biological materials and culture media to be stored or examined in the incubator 11. Enclosure materials that attenuate light of wavelength below about 500 nm are believed to be suitable for most applications. For particular applications it may be possible or necessary to use enclosure material having attentation thresholds at wavelength below or above 500 nm, respectively.

Figure 2:
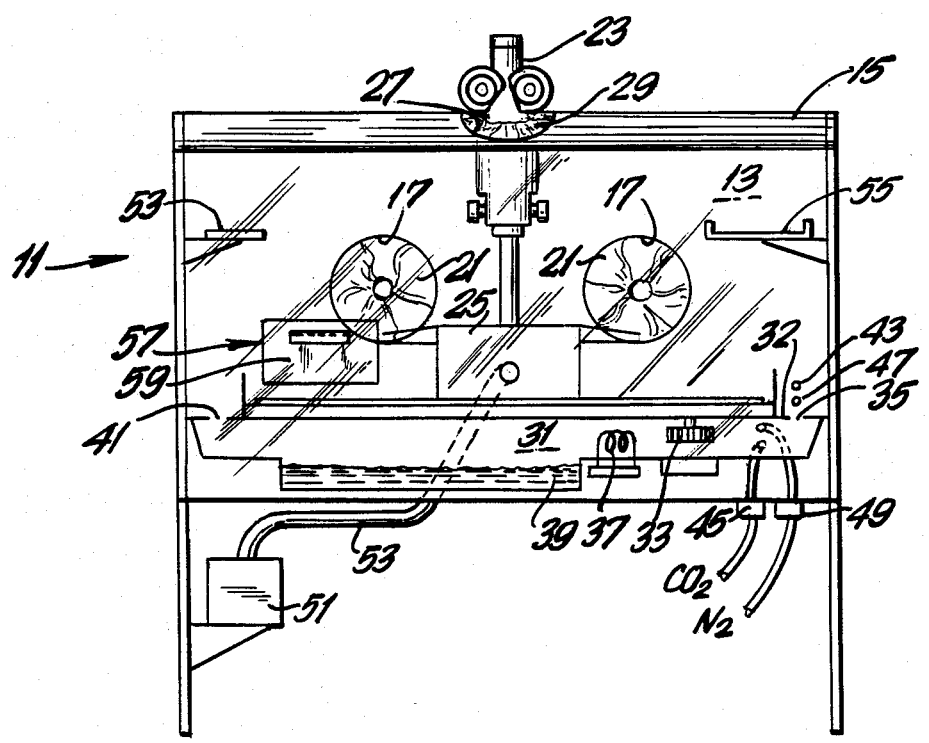
FIG. 2 is a front view of the preferred embodiment of an incubator in accordance with the invention.

FIG. 2 shows a front view of the interior of the incubator in accordance with the invention through the short wave length light attenuating transparent the front panel of enclosure 15. Access by user to the interior of the chamber 13 is provided by the hand openings 17 in the front face of the enclosure 15. Plastic cuffs 21 largely seal the hand openings 17 when not in use and seal the annulus between the user's wrist or forearm and the edge of the openings during use to prevent contamination of the atmosphere within the chamber 13 by ambient air. Typically, doors 19 (FIG. 1) are provided to completely seal the hand openings 17 when they are not in use.

In the illustrated embodiment a binocular microscope 23 is mounted on microscope stage 25 and extends through an aperture 27 in the top of the enclosure 15 for permitting the user to examine biological materials being maintained within the chamber 13. The annulus between the microscope 23 and the edge of the aperture 27 is sealed by a flexible plastic cuff 29.

Other hand openings may be provided in the back or side walls of the enclosure 15 as desired. Means such as flexible cuffs and doors should be provided to prevent a contamination of the atmosphere within the chamber 13. In addition, a door 28 in the rear of the chamber 13 (FIG. 3) permits the insertion of larger objects, such as the microscope 23 into the chamber 13. The door is normally kept closed and not used however, when the incubator 11 is in use. In some incubators the entire enclosure may be lifted off the base for easier access to the interior for purposes such as cleaning or installing of equipment.

The gas making up the atmosphere within the chamber 13 is circulated through humidification and temperature control chamber 31 located beneath the floor 32 of the chamber 13 by means of the fan 33. Gas from the chamber 13 is drawn through intake vents 35 in the floor 32 and heated by the thermostatically controlled heating coil 37. The actuation of the heating coil 37 may be controlled by a probe located in the chamber 13, for instance, on the microscope stage 25.

A high humidity is necessary within the chamber 13 to prevent excessive evaporation of the culture media in which the biological materials being maintained in the chamber are stored. In order to accomplish this the ambient gas, after passing through the heating coil 37, passes over a water reservoir 39 for humidification. Thereafter the gas passes through the outlet vents 41 back into chamber 13.

Most tissue culture media, including those for embryo growth, are formulated to be used in the presence of 5% $CO_2$, a concentration similar to that found in many tissues and biological fluids. In order to maintain the elevated 5% $CO_2$ concentration in the chamber 15, the $CO_2$ concentration is sensed by a sensor 43 which may, for instance, be an infrared detector of the type described in Chapter 10, of the book "Process Analyzer Technology" by Kenneth J. Clevett, John Wiley & Sons, 1986. When the $CO_2$ concentration falls below a preset level the sensor 43 causes a solenoid valve 45 to open to inject additional $CO_2$ into the chamber 13.

In accordance with the invention it has been found that the normal oxygen concentration in air (21%) is toxic to mouse zygotes and pre-embryos. Much fewer of those zygotes exposed to atmospheric levels of oxygen develop successfully and those that do continue to divide often do not progress past the stage normally observed at about 72 hours. If the oxygen level is reduced to 5-10% however, this inhibition is not observed and the embryos continue to develop. This effect has not heretofore been observed in human embryos, but it should be noted that such embryos are normally replaced within 48 hours which is before the toxic effects occuring in mouse embryos could be readily observed. It is believed that the use of air in the incubators of many "successful" IVF programs along with the exposure of eggs and embryos to air during their retrieval and examination, partially accounts for the relatively low success rates achieved in prior clinical programs (10-30% pregnancy rate).

To prevent the effects of oxygen toxicity the incubator in accordance with the invention injects nitrogen ($N_2$) into the chamber 13 whenever the oxygen concentration goes above a preset level in the range of about 5 to 10% $O_2$. The nitrogen purges out and replaces the oxygen until the proper preset level is reached. In the illustrated embodiment of the incubator 11 in accordance with the invention, this is accomplished by sensing the oxygen concentration in the gas in chamber 13 by means of sensor 47 within the chamber 13. The sensor 47 may, for instance, be a commercially available zirconium detector of the type described in Chapter 7 of the above referenced book "Process Analyzer Technology" or by a commonly used fuel cell detector. The zirconium detector is preferred because it is not sensitive to the humidity level within the chamber 13 or to the $CO_2$ concentration.

When the oxygen concentration falls below the preselected level in the illustrated embodiment of the invention the sensor 47 opens the solenoid valve 49 to inject additional carbon dioxide into the chamber 13 until the concentration of oxygen is reduced to the proper level. The oxygen sensor 47 and the nitrogen sensor 43 are preferably positioned in the chamber 13 upstream of the inlet vents 35 in the floor 32.

In certain applications it may be necessary to generate oxygen concentrations in the chamber 13 higher than in air or to add oxygen to the gas within the chamber to provide a more positive control of oxygen concentration. This may easily be accomplished in the incubator in accordance with the invention by providing an additional control for adding oxygen under the control of the sensor 47 or by replacing the nitrogen source with an oxygen source.

Most cultures of biological material are maintained at a temperature of about 37° C. and a 90-95% humidity. This temperature is the same as the body temperature for humans and embryos are, in fact, adversely affected by exposure to lower "room temperatures". It has been reported that a 15 minute exposure of exposure of oocytes (unfertilized eggs) to room temperature for as little as 10 minutes results in the disruption of the cellular apparatus (i.e. spindle fibers) which allows for the division of the chromosome during cellular division.

A high humidity is necessary to keep the tissue culture media from evaporating. This is especially important when using $CO_2$ and $N_2$ as in the incubator of the illustrated embodiment of the invention since these gases are bottled under extremely dry conditions and contain essentially no moisture. Consequently, in the absence of a humidification system the atmosphere within the chamber 13 would become very dry and evaporation of the warm culture media in the culture dishes would be significant. In the illustrated embodiment of the invention the $CO_2$ and $N_2$ are injected into the humidification and heating chamber 31 upstream from the fan 33. Therefore, before passing into the chamber 13 the injected gas is first heated by the heating coils 37 and humidified by passing over the water in the reservoir 39. If desired, apparatus could be provided for causing turbulence or atomization of water from the reservoir 39 in order to increase the humidification action. Alternative means of humidification, such as bubbling the gas through water may also be used.

Light for the microscope 23 is provided by light source 51 through the fiber optic cable 53. The light source 51 is provided with an amber or red filter such that the toxic short wave length components are eliminated from the light being supplied to the microscope 23. The light is delivered to the microscope stage 25 through fiber optic cable 53 in order to prevent the heat generated by light source 51 from adversely affecting the temperature regulation within the chamber 13.

The illustrated embodiment of the incubator 11 in accordance with the invention is provided with shelves 53 and 55 for storing things such as culture dishes within the chamber 13. In order to facilitate the circulation of gas within the chamber 13 it is preferable that the shelves 53 and 55 be perforated and that they be positioned with an appreciable gap between their edge and the adjacent wall of the enclosure 15.

Figure 3:
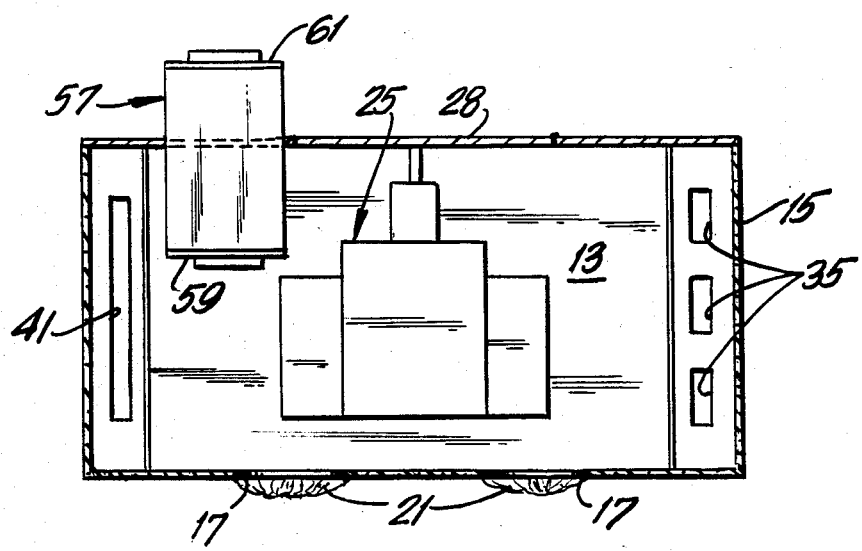
FIG. 3 is a top view of the incubator of FIG. 2.
Figure 7:
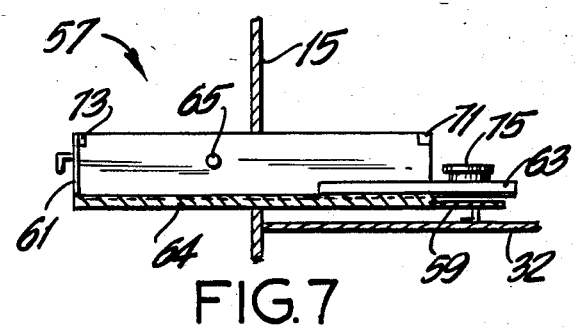
FIG. 7 is a detail side view of the airlock portion of the incubator of FIG. 2.
Figure 4:
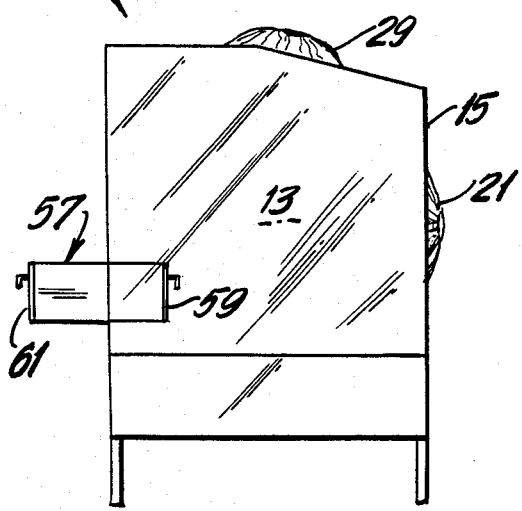
FIG. 4 is a left side view of the incubator of FIG. 2.
Figure 8:
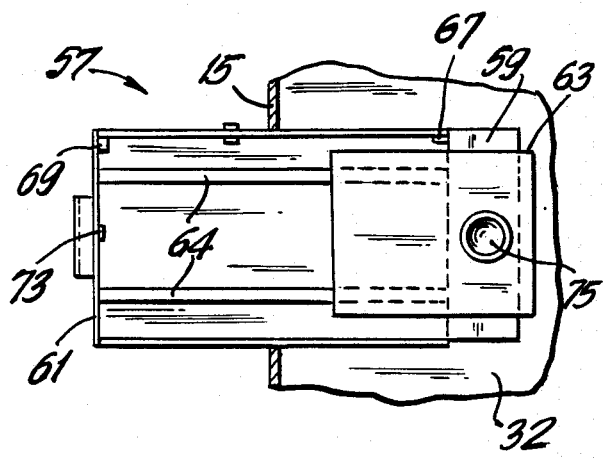
FIG. 8 is a top view of the airlock of FIG. 7.

It is important when dealing with zygotes and preembryos to maintain constant optimal gas environment within the chamber 13. During IVF procedures and the examination of embryos it is usually necessary to transfer culture dishes to or from the chamber 15. For instance, during a clinical procedure for the collection of eggs, culture dishes or tubes may be transferred as many as 20 to 40 times within 45 to 75 minutes. If, as in prior art incubators, this is done by means of opening and closing a door each time a culture dish is to be inserted or removed, undesirable loss of control of gas component concentrations, humidity and temperature levels are inevitable. It can take substantial amounts of time after a door is closed to restore the proper levels and $CO_2$ and $O_2$. This could have adverse effects on the wellbeing of biological materials in the chamber 15. Therefore, as seen in FIGS. 2, 3 and 4, there is provided an airlock 57 for allowing the easy transfer of biological materials in culture dishes and other equipment between the chamber 13 and the ambient. As best seen in FIGS. 7 and 8, the airlock 57 in the illustrated embodiment of the invention includes an internal door 59 and an external door 61 only one of which can be opened at a time. A tray 63 is slidably mounted on tracks 64 within the airlock 57. Stops (not shown) may be provided, for instance, on the floor of the airlock 57 to limit the extension of the tray 63 from the open end of the airlock 57.

The simultaneous opening of both doors 59 and 61 of the airlock is prevented in the illustrated embodiment by means of microswitches 67 and 69 and electrically activated latches 71 and 73. The opening of the interior airlock door 59 is sensed by the microswitch 67 which in turn activitates the latch 73 mounted on the interior top surface of the airlock 57 adjacent the exterior door 61. The actuation of the latch 73 locks the exterior door 51 in the closed position. When the interior door 59 is closed the microswitch 67 deactivates the latch 73 so that the exterior door 61 can be opened. The opening of the exterior door 61 is sensed by the microswitch 69, which in turn causes the latch 71 to lock the interior door 59 closed. When it is desired to insert a culture dish 75 into the chamber 13 the exterior door 61 of the airlock 57 is opened and the tray 63 is slidably extended from the airlock 57 for ease of placing culture dishes thereon. After the dishes are placed on the tray 63 the tray 63 is slid back within the airlock 57 and the door 61 is closed. Thereafter the user reaches through the hand openings 17 and opens the interior door 59 of airlock 57.

The tray 63 is then slid inwardly into the chamber 13 and the culture dishes 75 may be easily removed for placement on the microscope stage 25 or elsewhere within the chamber 13.

In order to prevent the airlock itself from becoming the source of the admission of atmospheric air to the chamber 13 gas inlet 65 may be provided in the airlock 57. Preferably commercially available premixed gas made up of, for example, 5% $O_2$, 5% $CO_2$, and 90% $N_2$ is infused into the airlock 57 through the connector 65.

Although the airlock 57 is shown in the illustrated embodiment as positioned in the back wall of the enclosure 15, it would be equally possible to position the airlock elsewhere, for instance, in the left side wall of the enclosure 15. The major constraint for the position of airlock 57 is that a user with hands extended through the hand openings 17 should be able easily to operate the interior portion of it.

Although the enclosure 15 in the illustrated embodiment of the incubator 11 in accordance with the invention has been described as being transparent, if desired, portions of it may be opaque and made out of materials other than plexiglass. For instance, the portion of the enclosure 13 below the floor 32 of the chamber 13 and the back wall of the enclosure 15 could be opaque and made, for instance, out of metal.

Figure 5:
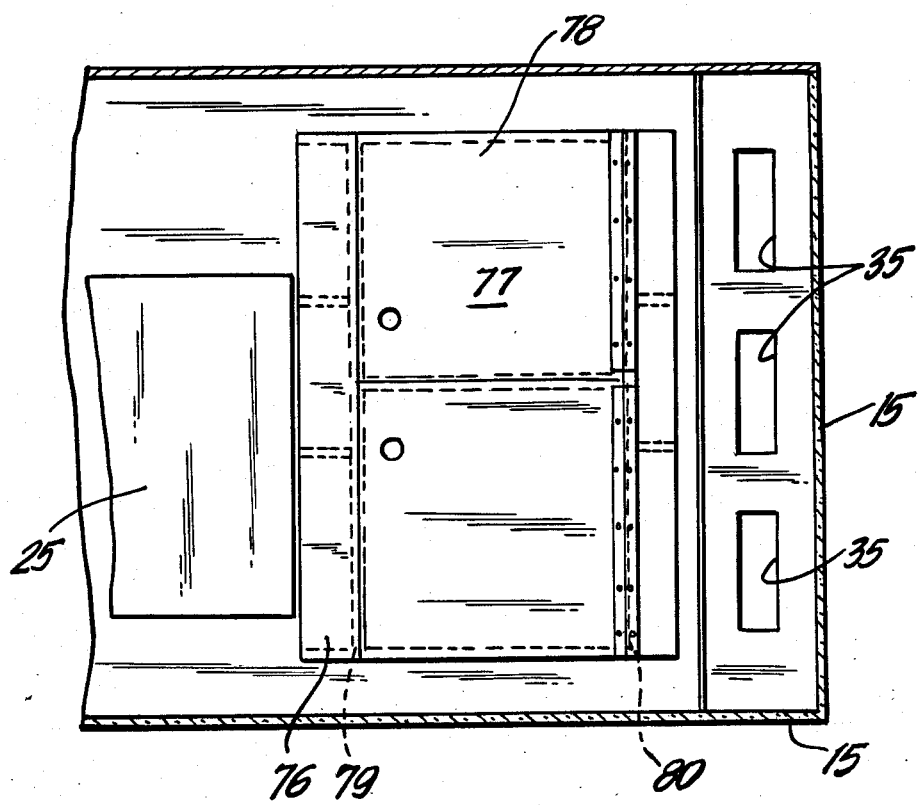
FIG. 5 is a top view of an interior storage container within the incubator of FIG. 2 which includes storage space.
Figure 6:
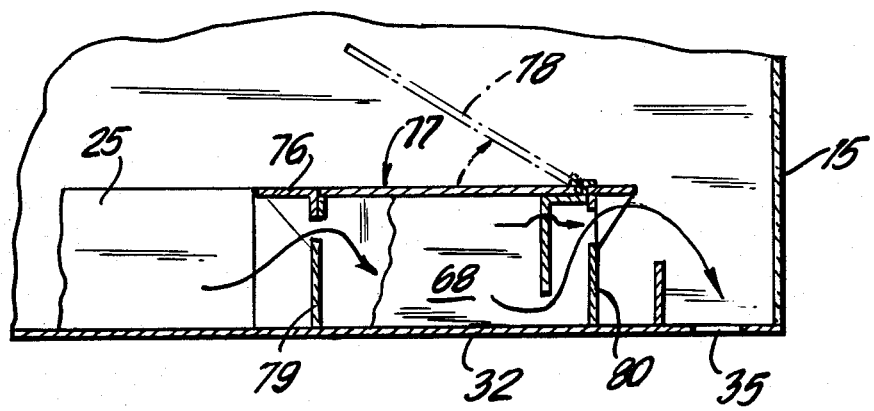
FIG. 6 is a side view of the storage container of FIG. 5.

In the embodiment of the incubator in accordance with the invention illustrated in FIGS. 5 and 6 of the drawings an interior platform and storage compartment 68 may be provided within the chamber 13 to the right of the microscope stage 25 for providing additional storage space for culture dishes and other items within the chamber 13. Preferably the top surface 76 of the platform 77 is at the same height as that of the microscope stage 25. The hinged top sections 78 of the platform 77 may be opened for access to the interior storage compartment. Apertures in the side walls 79 and 80 of the platform 77 permit circulation of gas through the interior of the platform for maintaining appropriate storage conditions.

While the invention has been described with relation to a particular illustrated embodiment, it should be recognized that various modifications can be made within the scope of the appended claims without departing from the spirit and scope of the invention. For instance, the walls of the incubator chamber could be flexible and other equipment could be placed within the chamber 13 in addition to or instead of a microscope.

We claim:

1. An environmentally controlled incubator, comprising:
   (a) an environmentally closed chamber including an enclosure having a transparent portion, said transparent portion including means for strongly attenuating transmission of light below a predetermined wavelength for preventing damage to culture media and biological materials within said chamber;
   (b) means for positioning a microscope stage having a microscope mounting thereon within said chamber;
   (c) a first aperture for permitting a microscope mounted on said stage to extend through said aperture;
   (d) second and third apertures within said enclosure positioned for allowing one using a microscope mounted on said microscope stage to manipulate things within said chamber, and sealing means for minimizing leakage between said chamber and the external ambient in the annuli between the edges of the said apertures and the microscope and forearms or hands of a user.

2. The incubator of claim 1 wherein said transparent portion of said enclosures strongly attenuates light having a wavelength of less than about 500 nm.

3. The incubator of claim 1 further including means for controlling the concentration of oxygen in the ambient gas within said chamber.

4. The incubator of claim 3 wherein said means for controlling the concentration of oxygen includes:
   (a) means for sensing the concentration of oxygen in said ambient gas; and
   (b) means for adding additional nitrogen to said ambient gas until the concentration of oxygen in said ambient gas reaches a predetermined level.

5. The incubator of claim 4 wherein said predetermined level is selected to be between about 5 to 10 percent.

6. The incubator of claim 1 further including an airlock for permitting objects to be placed within or removed from said chamber without modifying substantially the makeup of the ambient gas within said chamber.

7. The incubator of claim 6 wherein said airlock includes:
   (a) a cavity extending through said enclosure;
   (b) an internal door between said cavity and said chamber;
   (c) an external door between said cavity and the exterior of said chamber; and
   (d) means for permitting only one of said doors to be open at a time.

8. The incubator of claim 7 wherein said airlock further includes means for permitting the supply of gas of a selected composition to said cavity for maintaining the composition of the gas within said cavity to be similar to that of said ambient gas within said chamber.

9. The incubator of claim 4 wherein said airlock further includes a tray slidably mounted within said cavity for movement between position proximate the internal and external sides of said airlock.

10. An environmentally controlled incubator, comprising:
    (a) an environmentally closed chamber including an enclosure having a transparent portion;
    (b) means for positioning a microscope stage having a microscope mounted thereon within said chamber;
    (c) a first aperture for permitting a microscope mounted on said stage to extend through said aperture;
    (d) second and third apertures within said enclosure positioned for allowing one using a microscope mounted on said microscope stage to manipulate things within said chamber, and sealing means for minimizing leakage between said chamber and the external ambient in the annuli between the edges of the said apertures and the microscope and forearms or hands of a user.
    (e) means for sensing the concentration of oxygen in the ambient gas within said chamber; and
    (f) means responsive to the sensing by said sensing means of an oxygen concentration above a predetermined level for adding additional nitrogen to the ambient gas in said chamber for reducing said oxygen level to said predetermined level.

11. The incubator of claim 10 wherein said predetermined level is between about 5 to 10%.

12. The incubator of claim 10 further including an airlock for permitting objects to be placed within or removed from said chamber without modifying substantially the makeup of the ambient gas within said chamber.

13. The incubator of claim 12 wherein said airlock includes:
   (a) a cavity extending through the enclosure of the chamber;
   (b) an interior door between said cavity and said chamber;
   (c) an external door between said cavity and the exterior of said chamber; and
   (d) means for permitting only one of said doors to be open at a time.

14. The incubator of claim 10 further comprising:
   (a) a microscope stage;
   (b) an aperture in said enclosure positioned for permitting a microscope mounted on said stage to extend through said aperture for use by a user in studying biological materials within said chamber;
   (c) means for sealing the annulus between the edge of said aperture and said microscope.

15. The incubator of claim 14 further including a storage compartment for storing objects within said chamber and means for permitting circulation of ambient gas through said compartment.

16. The incubator of claim 5 further including means for controlling the concentration of carbon dioxide in the ambient gas within said chamber.

17. The incubator of claim 1 further including:
   (a) thermostatically controlled means for controlling the temperature of said ambient gas;
   (b) means for increasing the relative humidity of said ambient gas; and
   (c) means for circulating said ambient gas past said temperature controlling means and said humidity increasing means.

18. The incubator of claim 10 further including:
   (a) thermostatically controlled means for controlling the temperature of said ambient gas;
   (b) means for increasing the relative humidity of said ambient gas; and
   (c) means for circulating said ambient gas past said temperature controlling means and said humidity increasing means.

19. The incubator of claim 1 further including a storage compartment for storing objects within said chamber and means for permitting circulation of ambient gas through said compartment.

* * * * *